United States Patent [19]

Druker

[11] Patent Number: 4,502,011
[45] Date of Patent: Feb. 26, 1985

[54] RETAINING CLAMP FOR COMBINATION VALVE AND CONDUCTIVITY CELL ASSEMBLY

[75] Inventor: Harvey A. Druker, Bethel, Conn.

[73] Assignee: McNab Incorporated, Mount Vernon, N.Y.

[21] Appl. No.: 352,340

[22] Filed: Feb. 25, 1982

[51] Int. Cl.³ .............................................. G01N 27/02
[52] U.S. Cl. ................................................... 324/446
[58] Field of Search ....................... 324/446, 447, 450; 285/367; 356/440, 442

[56] References Cited

U.S. PATENT DOCUMENTS 2,377,510  6/1945  Newell .................................. 285/367
2,830,261  4/1958  Estelle .................................. 324/446

Primary Examiner—Michael J. Tokar
Assistant Examiner—Kevin D. O'Shea
Attorney, Agent, or Firm—Peck & Peck

[57] ABSTRACT

A retaining clamp for use with a combination valve and conductivity cell assembly is formed from two identical clamp halves which, when closed upon the valve and conductivity cell assembly, tightly connects the valve nipple and operating safety nut of the assembly in fixed operating relationship to insure proper reciprocal movement of the valve sleeve.

4 Claims, 5 Drawing Figures

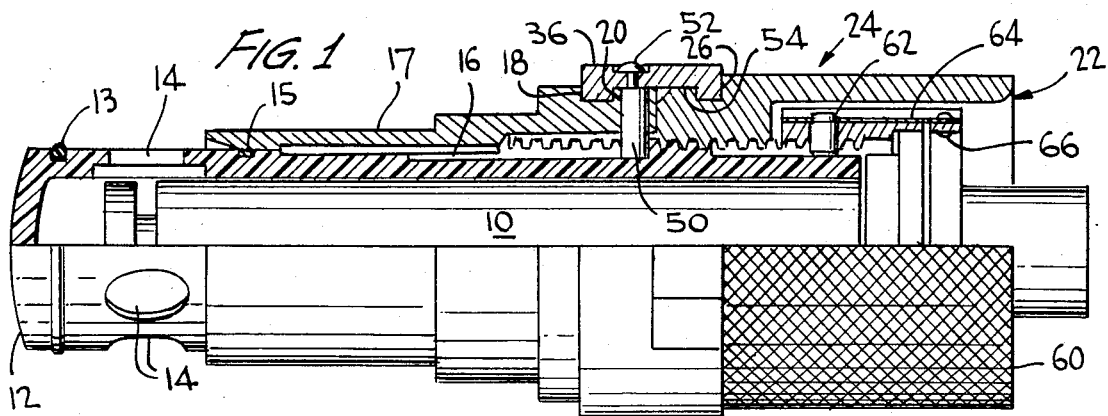
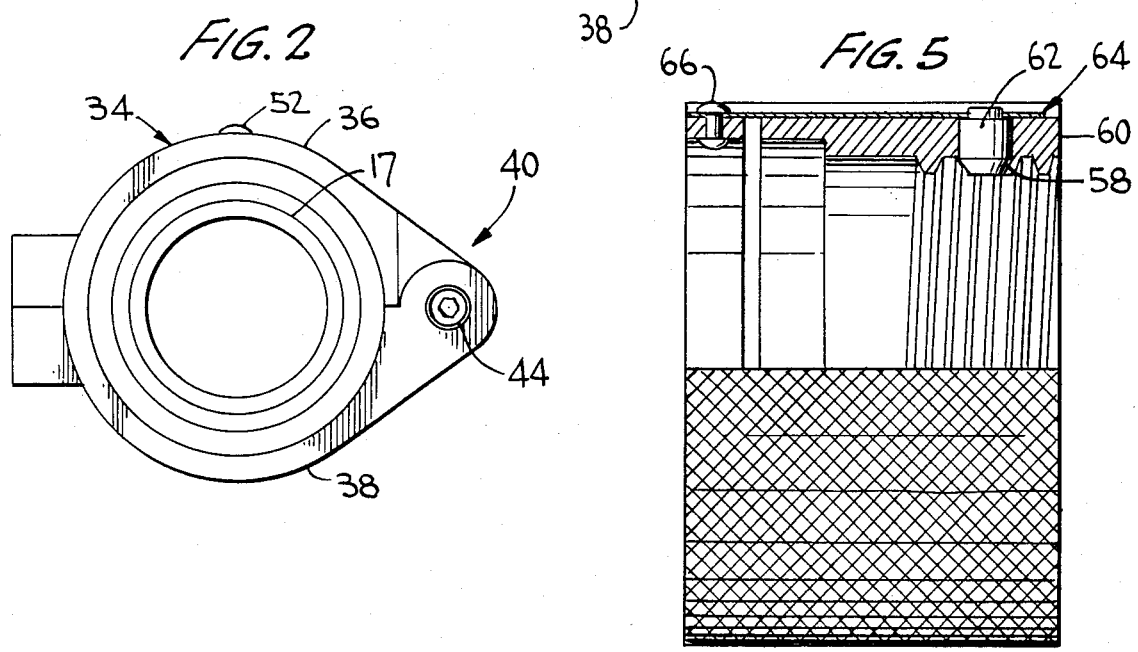
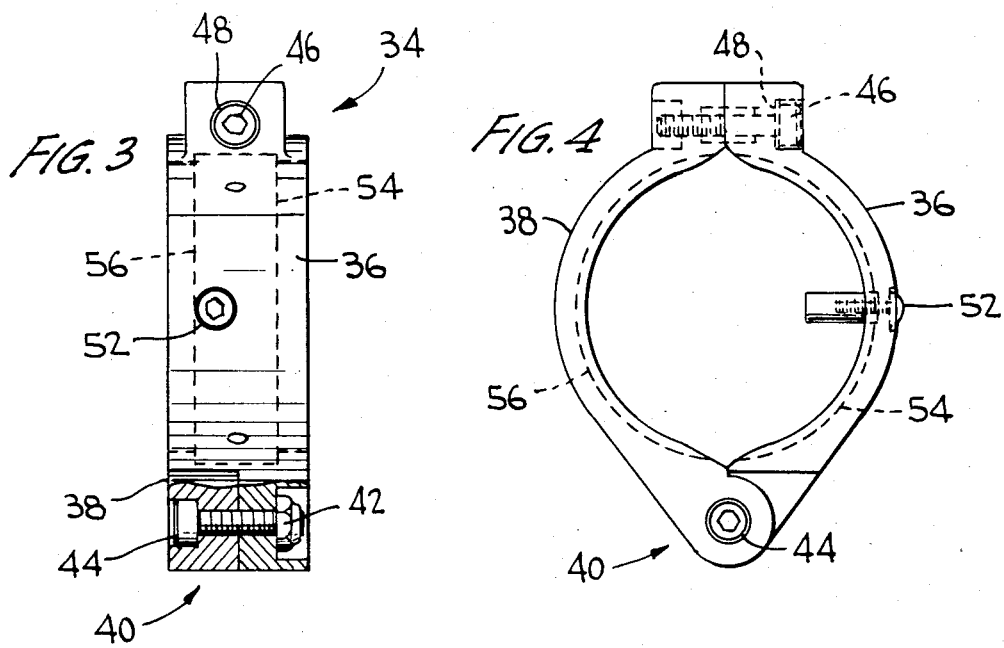

RETAINING CLAMP FOR COMBINATION VALVE AND CONDUCTIVITY CELL ASSEMBLY

BACKGROUND OF THE INVENTION

The present invention generally appertains to improvements in a combination valve and conductivity cell assembly and especially relates to a retaining clamp for maintaining the parts of such assembly in a fixed, operating relationship.

Combination valve and conductivity cell assemblies generally comprise a conductivity cell mounted in operative position so that the electrodes thereof are projected into a liquid flow conduit through an opening therein. Such assemblies include a valve whereby the conductivity cell may be retracted from operative position within the liquid flow conduit for replacement and/or repair while, at the same time, the valve is actuated to close the opening in the liquid flow conduit in order to prevent escape of liquid therefrom. Such a combination valve and conductivity cell assembly is disclosed in U.S. Pat. No. 2,830,261.

In actual practice it has been found that the electrodes must be replaced or cleaned or repairs made thereto or to the cell at relatively frequent intervals as they become corroded and otherwise incapable of properly performing their measuring function. When it is necessary to replace or otherwise repair the electrodes or any other elements or parts of the conductivity cell or assembly, it will be obvious that great savings in time, labor and parts can be made by reducing the number of parts which must be removed and/or replaced.

In designing such combination valve and conductivity cell assemblies, it is important to provide for operator safety while, at the same time, reducing the number of parts required to install the entire cell assembly, thereby reducing the factors of human error, installation time, labor and lost parts. In prior assemblies such as disclosed in U.S. Pat. No. 2,830,261, FIG. 8, the operating safety nut (191) was maintained in assembly with the nipple valve (171) by a retaining clamp comprised of two half-round retaining rings (189), a retaining sleeve (187), a screw (194) and a retaining pin (195) for limiting the extremes of motion of the valve inner-body (175). The present invention, in addition to other objects and features to be described, has a single piece retaining clamp assembly which replaced the several components aforementioned and which enhances operator safety, reduces installation time, labor and lost parts.

SUMMARY OF THE INVENTION

The present invention provides a novel retaining clamp assembly which replaces several components of presently known combination valve and conductivity cell assemblies by a single piece assembly having two identical halves which are hinged at one point to form a closeable clamp having fixed pin means therein whereby the retaining clamp can be installed as a single operation to maintain the operating safety nut in assembly with the valve nipple.

It is the object of the present invention to provide a retaining clamp assembly for use in prior art combination valve and conductivity cell assemblies whereby operator safety will be enhanced and the number of parts will be reduced thereby reducing human error, installation time, labor and lost parts.

It is further the object of the present invention to provide an improved combination valve and conductivity cell assembly which reduces or eliminates the buildup of salts and corrosive elements that develop on such valve assemblies.

It is a further object of the present invention to provide a combination valve and conductivity cell assembly having safety means for insuring that the valve must be in a closed position before the conductivity cell may be removed from the conduit.

It is a further object of the present invention to provide an assembly having a valve sleeve head of great strength to resist the effect of water hammer.

BRIEF DESCRIPTION OF THE DRAWINGS

FIG. 1 is a view in longitudinal section of a combination valve and conductivity cell assembly having the retaining clamp of the present invention mounted thereon.

FIG. 2 is an end view of the apparatus shown in FIG. 1.

FIG. 3 is a side elevation view of the retaining clamp of the present invention.

FIG. 4 is an end view of the retaining clamp shown in FIG. 3.

FIG. 5 is a view in longitudinal section of the safety means which prevent removal of the conductivity cell while the valve is in open position.

DESCRIPTION OF A PREFERRED EMBODIMENT

Referring now to the accompanying drawings, particularly FIG. 1 thereof, I have illustrated a combination valve and conductivity cell assembly useful with the retaining clamp assembly of the present invention.

The valve is to be mounted in a housing as disclosed in Estelle U.S. Pat. No. 2,830,261. The valve comprises a sleeve or inner-body 10 having a valve-sleeve head 12, constructed of a non-metallic material such as a plastic polyethersulfone material, which is dome-shape as shown, and located on the front or forward end of the valve sleeve. Located rearwardly of the valve head is a circumferential groove containing a sealing or "O" ring 13 of rubber seated therein.

The valve sleeve is formed at its forward end with openings or apertures 14 extending through the walls thereof. Located rearwardly of the apertures 14 is a second circumferential groove having a sealing ring 15 seated therein. An axial slot 16 extends along part of the length of valve sleeve 10.

A valve nipple 17 is threadedly mounted on the valve sleeve 10. Valve nipple 17 has a forward portion which may be externally threaded (not shown) for attachment to a threaded union as is well known. Valve nipple 17 has a rear portion having a nipple flange 18, and rearwardly of said flange, a slot 20.

An operating safety nut 22 is threadedly mounted on the valve sleeve 10 as is well known. Operating safety nut 22 has a forward portion, indicated generally at 24, having a flange 26 therein. Operating safety nut 22 has a rear retaining nut portion genenerally indicated at 28.

A co-axial conductivity cell 30 is mounted within the valve sleeve 10 in a manner well known and is maintained in position by a cell retaining nut assembly, indicated generally at 32, as described hereinafter.

Referring now to FIGS. 1 through 4, the retaining clamp assembly of the present invention comprises a clamp generally indicated at 34, having two identical halves 36 and 38, which are sized and shaped to fit around and receive the valve and conductivity cell assembly. The clamp has a hinge, generally indicated at 40 having a locking nut 42 installed in one of the halves and a screw 44 for engaging the locking nut in the other half. The locking nut prevents either tightening or loosening of the hinge thus formed, thereby maintaining free operating action of the clamp. The clamp has a screw 46 and lock washer 48 for securing and maintaining the clamp in a closed position. A retaining pin 50 extends inwardly from half 36 and is secured thereto by a screw 52.

The halves 36 and 38 of the clamp 34 have internally recessed portions forming flanges indicated by the lines 54 and 56 (FIGS. 3 and 4). These clamp flanges are adapted to engage the flanges 18 and 26 on the valve nipple 16 and operating safety nut 22, respectively.

The retaining clamp assembly of the present invention is useful with a combination valve and conductivity cell assembly by placing the clamp 34 in position with the valve and cell assembly whereby the clamp retaining pin 50 mates with the nipple flange slot 20 and the clamp flanges fit over the respective flanges of both the valve nipple 17 and operating safety nut 22. The opposing half of clamp 34 is then rotated until both halves contact, whereupon the captive screw 46 is tightened to secure and maintain the clamp in a closed condition.

Referring now to FIG. 1 and, more particularly, FIG. 5, there are illustrated the means which prevent removal of the conductivity cell from its operative mounted position within the valve when the valve is in its open position. The structure insures that when the valve is in its open position, the cell retaining nut is inoperable to allow removal of the conductivity cell.

The valve sleeve 10 has a groove 58 (FIG. 1) located at the rear extremity thereof. The cell retaining nut assembly 32 (FIG. 1) comprises a retaining nut 60 (FIG. 5), a moveable safety pin 62 and a leaf spring 64 which is surface mounted on retaining nut 60 by means of a rivet 66. The leaf spring and safety pin are adapted to co-act by urging the safety pin inwardly from the surface of retaining nut 60. When the retaining nut 60 is properly tightened to fix conductivity cell 30 in operative position within valve sleeve 10, the safety pin 62 will drop into the valve sleeve groove 58. As the operating safety nut 22 is rotated to axially move valve sleeve 10 into the liquid flow conduit (not shown), the rear retaining nut portion 28 of the operating safety nut 22 is positioned above the safety pin 62, whereby the safety pin may not be removed from the groove 58. If an attempt is made to turn cell retaining nut 60 so as to release and remove the conductivity cell 30, the safety pin 62, which is engaged in valve sleeve groove 58 so as to be immovable, prevents the cell retaining nut 60 from moving. The safety pin 62 cannot be withdrawn from the groove 58 until the operating safety nut 22 is rotated clear of the safety pin 62. Thus, the valve sleeve 10 must be fully withdrawn from the conduit and in a safe position before the cell retaining nut 60 can be turned.

It will be appreciated that the present invention is a novel retaining clamp assembly which is useful with combination valve and conductivity cells to accomplish the objects of enhancing operator safety, reducing the number of parts required to install and maintain the entire cell assembly so as to reduce the possibility of human error, installation time, labor and lost parts.

The present invention has the desirable feature of greatly reducing or eliminating the buildup of salts and corrosive elements that commonly develop on such valve assemblies by utilizing a plastic molded unit comprised of polyethersulfone material for the valve sleeve 10. Since the valve sleeve is not metallic, it is not subject to electrolytic and galvanic corrosion associated with dissimilar metals. Thus, the likelihood of valve failure due to corrosion or impaction due to accumulation of corrosive elements is minimized or eliminated.

Another desirable feature of the present invention is the introduction of a dome shaped head for the valve sleeve 10. This dome shaped head provides great strength for the valve sleeve needed to resist the effect of water hammer.

A further desirable feature of the present invention is the provision of a simple locking means whereby the cell reatining nut assembly will be immovable when the valve is in its open position, thereby insuring that the conductivity cell will not be removed when the valve is open.

What is claimed is:

1. A valve and conductivity cell assembly comprising a housing adapted to be mounted on and in communication with a liquid flow conduit containing a liquid to be tested, a valve sleeve of plastic material reciprocably mounted in said housing and having a head in contact with the liquid in the flow conduit, a valve nipple mounted on the valve sleeve for reciprocation thereof, an operating safety nut for reciprocating said valve sleeve and valve nipple to and from a closed position, a conducticity cell removably mounted in said valve sleeve for reciprocation therewith and in testing contact with the liquid when the valve sleeve is in open position, a clamp having identical first and second halves each having inwardly facing flanges formed on the inner surface thereof, said valve nipple and operating safety nut having laterally outwardly projecting flanges arranged in facial confronting relation and cooperatively engaged by the inwardly facing flanges on the inner surfaces of the clamp halves, one end of each half of the clamp being attached to form a hinge for free swinging action between said halves, the other ends of said halves being releasably fixed to maintain said clamp in a closed position, said flanges being relieved adjacent the releasably fixed ends with the inner radius being reversed, retaining pin means fixedly mounted on one of said halves and extending inwardly therefrom, whereby when said clamp is mounted on said valve assembly the flanges on said clamp will engage said valve nipple and said operating safety nut without damaging the same and retain the same connected and said retaining pin will engage said valve sleeve whereby said valve nipple and said operating safety nut will be maintained in fixed position relationship during reciprocation of said valve sleeve.

2. The invention of claim 1 and including means for preventing removal of the conductivity cell from its operative mounted position within the valve sleeve when the valve sleeve is in its open position, said means including a groove in the valve sleeve, a retaining nut encircling said valve sleeve and the groove and having a radially movable safety pin for engagement with the valve sleeve groove, a leaf spring having an end fixedly mounted on the surface of the retaining nut and having a free end overlying the safety pin and urging the same inwardly and preventing accidental withdrawal thereof from the retaining nut.

3. The invention of claim 1 wherein said valve sleeve is formed from polyethersulfone.

4. The invention of claim 1 wherein said head on the valve sleeve is dome shaped to provide strength therefor in respect to the flowing liquid in the flow conduit.

* * * * *